(12) United States Patent
Fabry et al.

(10) Patent No.: US 11,338,106 B2
(45) Date of Patent: May 24, 2022

(54) HEARING ASSISTANCE DEVICES WITH MOTION SICKNESS PREVENTION AND MITIGATION FEATURES

(71) Applicant: Starkey Laboratories, Inc., Eden Prairie, MN (US)

(72) Inventors: David Alan Fabry, Eden Prairie, MN (US); Justin R. Burwinkel, Eden Prairie, MN (US); Jeffery Lee Crukley, Milton (CA); Kenneth Kragh Jensen, Brunswick, MD (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 50 days.

(21) Appl. No.: 16/803,639

(22) Filed: Feb. 27, 2020

(65) Prior Publication Data

US 2020/0269008 A1    Aug. 27, 2020

Related U.S. Application Data

(60) Provisional application No. 62/811,367, filed on Feb. 27, 2019.

(51) Int. Cl.
*A61B 3/113*    (2006.01)
*A61B 5/11*    (2006.01)
(Continued)

(52) U.S. Cl.
CPC .............. *A61M 21/00* (2013.01); *A61B 3/113* (2013.01); *A61B 5/1114* (2013.01);
(Continued)

(58) Field of Classification Search
CPC .... H04R 25/00–75; H04R 2225/00–83; H04R 2460/00–17; A61M 21/00–02;
(Continued)

(56) References Cited

U.S. PATENT DOCUMENTS

| 9,167,356 B2 | 10/2015 | Higgins et al. |
| 2007/0034212 A1 | 2/2007 | Brendley et al. |

(Continued)

FOREIGN PATENT DOCUMENTS

WO    2020176770    9/2020

OTHER PUBLICATIONS

"International Search Report and Written Opinion," for PCT Application No. PCT/US2020/020168 dated Jun. 17, 2020 (19 pages).
(Continued)

*Primary Examiner* — Thaddeus B Cox
(74) *Attorney, Agent, or Firm* — Pauly, DeVries Smith & Deffner LLC

(57) ABSTRACT

Embodiments herein relate to devices and related systems and methods for motion sickness prevention and mitigation. In an embodiment, a method of preventing or mitigating motion sickness in a subject is included, the method tracking motion of the subject using a first motion sensor; estimating a vestibular system input based on tracked motion of the subject; tracking head position of the subject using the first motion sensor; estimating a visual system input based on tracked head position of the subject; estimating consistency between the vestibular system input and the visual system input; and initiating a responsive measure if the estimated consistency crosses a threshold value. Other embodiments are also included herein.

23 Claims, 10 Drawing Sheets

(51) Int. Cl.
  *H04R 25/00* (2006.01)
  *A61M 21/00* (2006.01)
  *A61B 5/00* (2006.01)

(52) U.S. Cl.
  CPC .......... *A61B 5/4023* (2013.01); *A61B 5/4211* (2013.01); *A61B 5/486* (2013.01); *A61B 5/4836* (2013.01); *A61B 5/7278* (2013.01); *H04R 25/554* (2013.01); *A61B 2560/0257* (2013.01); *A61B 2562/0204* (2013.01); *A61B 2562/0219* (2013.01); *A61B 2562/0223* (2013.01); *A61M 2021/005* (2013.01); *A61M 2021/0027* (2013.01); *A61M 2021/0066* (2013.01); *A61M 2230/63* (2013.01)

(58) Field of Classification Search
  CPC ........ A61M 2230/62–63; A61B 5/1114; A61B 5/1123; A61B 5/4023
  See application file for complete search history.

(56) References Cited

U.S. PATENT DOCUMENTS

| | | |
|---|---|---|
| 2009/0002142 A1 | 1/2009 | Morimoto et al. |
| 2012/0219180 A1 | 8/2012 | Mehra |
| 2014/0002586 A1 | 1/2014 | Nourbakhsh |
| 2014/0176296 A1 | 6/2014 | Morgan |
| 2015/0002808 A1 | 1/2015 | Rizzo, III et al. |
| 2018/0228404 A1 | 8/2018 | Bhunia et al. |
| 2018/0317837 A1 | 11/2018 | Burwinkel et al. |
| 2018/0365804 A1* | 12/2018 | Rikoski .................. G09G 5/003 |
| 2019/0043232 A1 | 2/2019 | Appakutty |
| 2019/0047498 A1* | 2/2019 | Alcaidinho ............... G06F 3/14 |
| 2020/0337623 A1* | 10/2020 | Bulut .................... G16H 20/30 |

OTHER PUBLICATIONS

"International Preliminary Report on Patentability," for PCT Application No. PCT/US2020/020168 dated Sep. 10, 2021 (11 pages).

* cited by examiner

HEARING ASSISTANCE DEVICES WITH MOTION SICKNESS PREVENTION AND MITIGATION FEATURES

This application claims the benefit of U.S. Provisional Application No. 62/811,367, filed Feb. 27, 2019, the content of which is herein incorporated by reference in its entirety.

FIELD

Embodiments herein relate to devices and related systems and methods for motion sickness prevention and mitigation. More specifically, embodiments herein relate to hearing assistance devices with motion sickness prevention and mitigation features.

BACKGROUND

The brain receives various inputs that can indicate motion. Motion can be sensed primarily by the body's vestibular system and visual system, and to a lesser extent by other systems such as the somatosensory and proprioceptive systems. The brain synthesizes received inputs to provide appropriate sensations with respect to movement. For example, when a person is walking, the various inputs to the brain are typically highly consistent with one another and result in an appropriate sensation of movement.

However, in some individuals or situations, received vestibular and visual inputs are not consistent with one another. These inconsistent inputs can lead to sensations and symptoms associated with motion sickness. Inconsistent inputs can be caused by particular activities, disease states, impairments, or the like.

Inconsistent vestibular and visual inputs received by the brain can cause motion sickness in some people. Motion sickness may result in nausea, vomiting, dizziness, malaise, headache, pallor, palpitations, anxiety, fatigue, difficulty maintaining balance, unsteadiness, impaired cognitive function and the like.

One example of an activity leading to inconsistent vestibular and visual inputs is an individual riding in a car with their gaze down on a stationary object (stationary in a frame relative to the vehicle) such as a book. In such a case, their vestibular system will still provide an input to the brain that is consistent with motion. However, with their gaze down on the book, their visual system will not be providing an input that indicates motion.

SUMMARY

Embodiments herein relate to devices and related systems and methods for motion sickness prevention and mitigation. In an embodiment, a method of preventing or mitigating motion sickness in a subject is included. The method can include tracking motion of the subject using a first motion sensor, estimating a vestibular system input based on tracked motion of the subject, tracking head position of the subject using the first motion sensor, estimating a visual system input based on tracked head position of the subject, estimating consistency between the vestibular system input and the visual system input, and initiating a responsive measure if the estimated consistency crosses a threshold value.

In an embodiment, a method of preventing or mitigating motion sickness in a subject is included herein, the method including tracking motion of the subject using a first motion sensor associated with a hearing assistance device, tracking head position of the subject using the first motion sensor, capturing ambient sounds with the hearing assistance device, classifying the surroundings based on the tracked motion, tracked head position, and ambient sound as one of vehicular, stationary, and non-stationary, and initiating a responsive measure based on the classification of the surroundings.

In an embodiment, a motion sickness prevention system is included having a first control circuit and a first motion sensor in electrical communication with the first control circuit. The first motion sensor can be disposed in a fixed position relative to a head of a subject wearing the hearing assistance device. The system can further include a first microphone in electrical communication with the first control circuit, a first electroacoustic transducer for generating sound in electrical communication with the first control circuit, and a first power supply circuit in electrical communication with the first control circuit. The first control circuit can be configured to track motion of the subject using the first motion sensor, estimate vestibular system input based on tracked motion of the subject, track head position of the subject using the first motion sensor, and estimate visual system input based on tracked head position of the subject.

In an embodiment, a motion sickness prevention system is included having a first control circuit and a first motion sensor in electrical communication with the first control circuit. The first motion sensor can be disposed in a fixed position relative to a head of a subject wearing the hearing assistance device. The system can further include a first microphone in electrical communication with the first control circuit, a first electroacoustic transducer for generating sound in electrical communication with the first control circuit, and a first power supply circuit in electrical communication with the first control circuit. The first control circuit can be configured to track motion of a subject using the motion sensor, track head position of a subject using the motion sensor, sense vibrations with a vibration sensor, sense ambient sounds with the microphone, and sense magnetic fields with a magnetic field sensor. The first control circuit can be configured to classify the surroundings based on the tracked motion, tracked head position, sensed vibrations, sensed ambient sound, and sensed magnetic fields, as one of as one of vehicular, stationary, and non-stationary. The first control circuit can be further configured to initiate a responsive measure based on the classification of the surroundings.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As described above, inconsistent vestibular system and visual system inputs can lead to motion sickness. In accordance with various embodiments herein, systems and methods are provided by preventing and/or mitigating motion sickness in a subject.

In various embodiments herein, a system such as a hearing assistance device can track the motion or movement of a subject using a motion sensor. In some embodiments, the system can estimate vestibular system input based on the tracked motion of the subject. The head position of the subject can also be tracked. In some embodiments, the system can estimate visual system input based on the tracked head position. The system can estimate consistency between or otherwise compare the vestibular system inputs and the visual system inputs. In various embodiments, the system can also initiate responsive measures if the estimated consistency crosses a threshold value.

The term "motion sickness" as used herein shall include reference to sea sickness, air sickness, travel sickness, space sickness, screen sickness and virtual reality stimulation sickness, unless the context dictates otherwise.

The term "hearing assistance device" as used herein shall refer to devices that can aid a person with impaired hearing. The term "hearing assistance device" shall also refer to devices that can produce optimized or processed sound for persons with normal hearing. The term "hearing assistance device" shall also refer to devices worn on or about the ear, and that may produce sound or perform other useful functions for the user. Hearing assistance devices herein can include hearables (e.g., wearable earphones, headphones, earbuds, virtual reality headsets), hearing aids (e.g., hearing instruments), cochlear implants, and bone-conduction devices, for example. Hearing assistance devices include, but are not limited to, behind-the-ear (BTE), in-the ear (ITE), in-the-canal (ITC), invisible-in-canal (IIC), receiver-in-canal (RIC), receiver in-the-ear (RITE) or completely-in-the-canal (CIC) type hearing assistance devices or some combination of the above.

Figure 1:
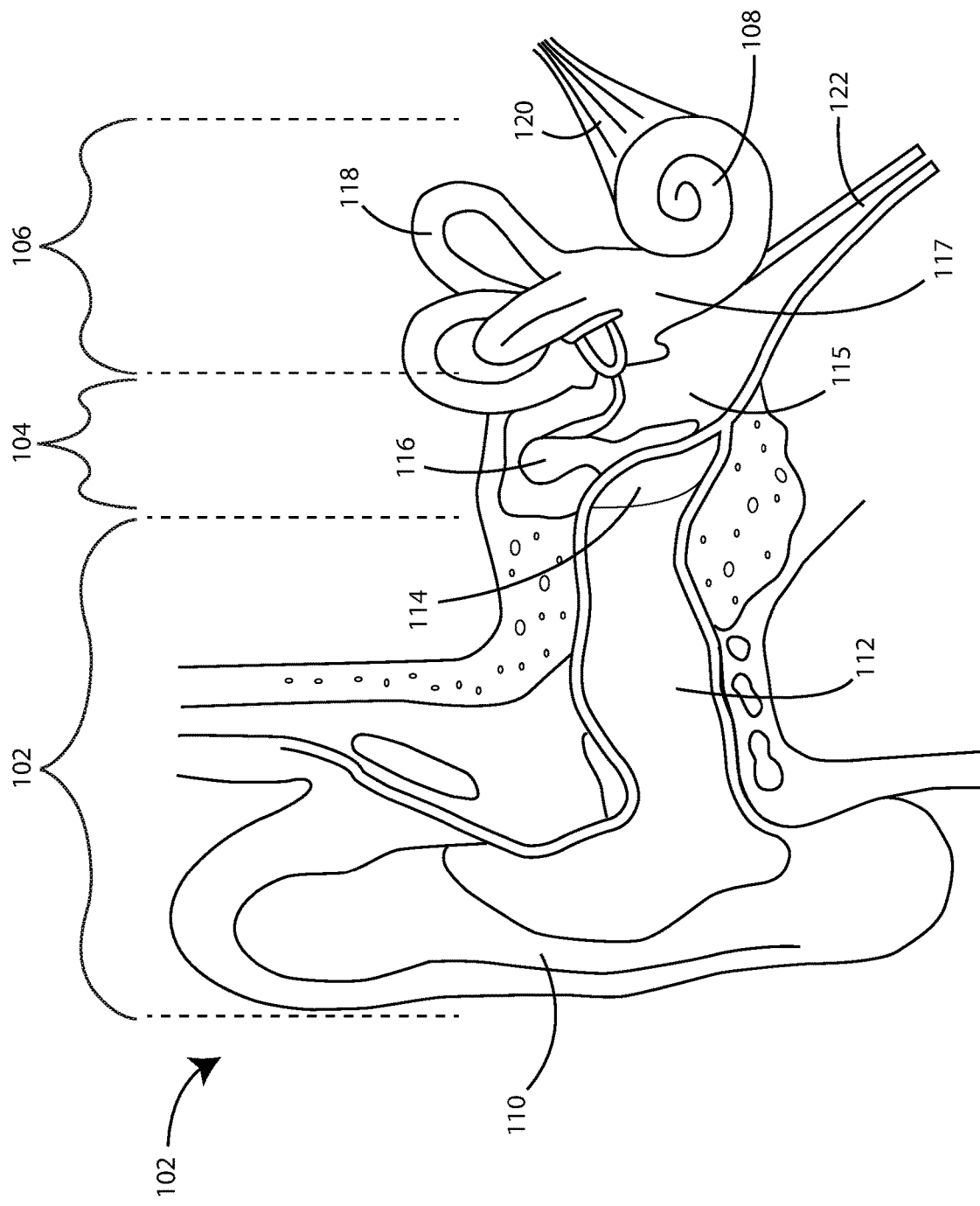
FIG. 1 is a partial cross-sectional view of ear anatomy.

Referring now to FIG. 1, a partial cross-sectional view of ear anatomy 100 is shown. The three parts of the ear anatomy 100 are the outer ear 102, the middle ear 104 and the inner ear 106. The inner ear 106 includes the cochlea 108, vestibule 117, the semicircular canals 118, and cranial nerve VIII (the vestibulocochlear/auditory nerve) 120. The outer ear 102 includes the pinna 110, ear canal 112, and the tympanic membrane 114 (or eardrum). The middle ear 104 includes the tympanic cavity 115 and auditory bones 116 (malleus, incus, stapes). The pharyngotympanic tube 122 (i.e., the eustachian tube) is an air pathway in communication with the middle-ear space and nasopharynx. The eustachian tube helps to control pressure within the middle ear space, generally making it equal with, e.g., ambient air pressure.

Sound waves enter the ear canal 112 and make the tympanic membrane 114 vibrate. This action oscillates the tiny chain of auditory bones 116 (ossicles—malleus, incus, stapes) in the middle ear 104. The medial bone in this chain contacts the oval window membrane of the cochlea 108 and transfers the oscillations to the fluid in the cochlea 108. The three ossicles (i.e., ossicular chain) create a lever action and help to overcome the air-to-fluid impedance miss-match along the air-conduction auditory pathway. The fluid movement eventually results in a neural response along the auditory nerve 120.

Hearing assistance devices, such as hearing aids and hearables (e.g., wearable earphones), can include an enclosure, such as a housing or shell, within which internal components are disposed. Components of a hearing assistance device herein can include a control circuit, digital signal processor (DSP), memory (such as non-volatile memory), power management circuitry, a data communications bus, one or more communication devices (e.g., a radio, a near-field magnetic induction device), one or more antennas, one or more microphones, a receiver/speaker, and various sensors as described in greater detail below. More advanced hearing assistance devices can incorporate a long-range communication device, such as a BLUETOOTH® transceiver or other type of radio frequency (RF) transceiver.

Figure 2:
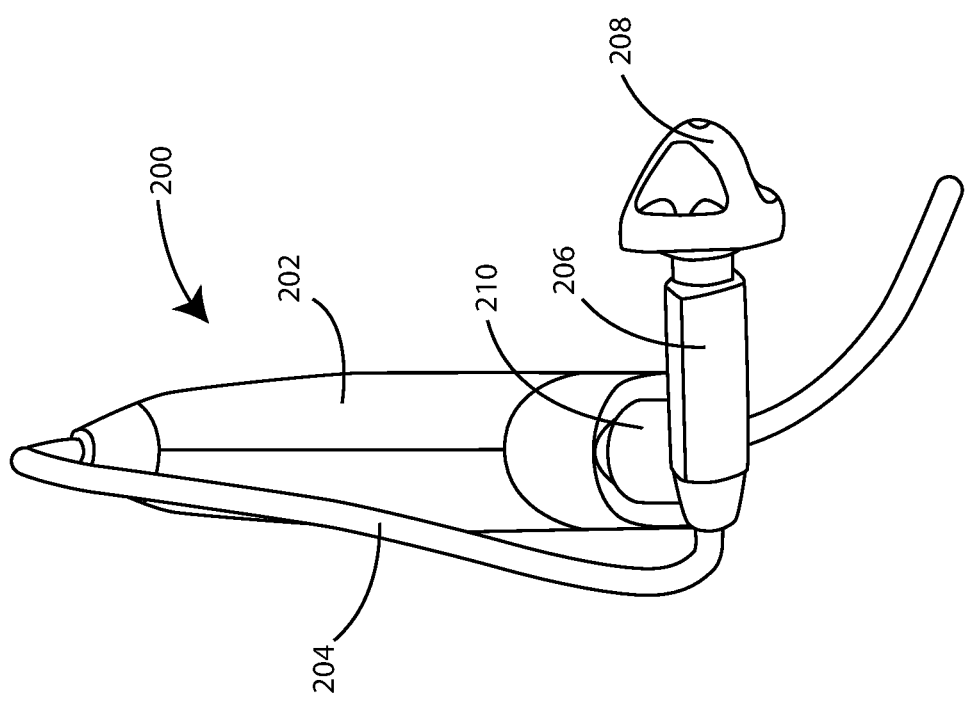
FIG. 2 is a schematic view of a hearing assistance device in accordance with various embodiments herein.

Referring now to FIG. 2, a schematic view of a hearing assistance device 200 is shown in accordance with various embodiments herein. The hearing assistance device 200 can include a hearing device housing 202. The hearing device housing 202 can define a battery compartment 210 into which a battery can be disposed to provide power to the device. The hearing assistance device 200 can also include a receiver 206 adjacent to an earbud 208. The receiver 206 an include a component that converts electrical impulses into sound, such as an electroacoustic transducer, speaker, or loud speaker. A cable 204 or connecting wire can include one or more electrical conductors and provide electrical communication between components inside of the hearing device housing 202 and components inside of the receiver 206.

The hearing assistance device 200 shown in FIG. 2 is a receiver-in-canal type device and thus the receiver is designed to be placed within the ear canal. However, it will be appreciated that many different form factors for hearing assistance devices are contemplated herein. As such, hearing assistance devices herein can include, but are not limited to, behind-the-ear (BTE), in-the ear (ITE), in-the-canal (ITC), invisible-in-canal (IIC), receiver-in-canal (RIC), receiver in-the-ear (RITE), completely-in-the-canal (CIC) type hearing assistance devices, cochlear implants, and osseo-integrated/bone-conduction type devices.

Hearing assistance devices of the present disclosure can incorporate an antenna arrangement coupled to a high-frequency radio, such as a 2.4 GHz radio. The radio can conform to an IEEE 802.11 (e.g., WIFI®) or BLUETOOTH® (e.g., BLE, BLUETOOTH® 4, 2 or 5.0) specification, for example. It is understood that hearing assistance devices of the present disclosure can employ other radios, such as a 900 MHz radio. Hearing assistance devices of the present disclosure can be configured to receive streaming audio (e.g., digital audio data or files) from an electronic or digital source. Representative electronic/digital sources (also referred to herein as accessory devices) include an assistive listening system, a TV streamer, a radio, a smartphone, a cell phone/entertainment device (CPED), remote control, or other electronic device that serves as a source of digital audio data, setting configurations, commands, or files.

Figure 3:
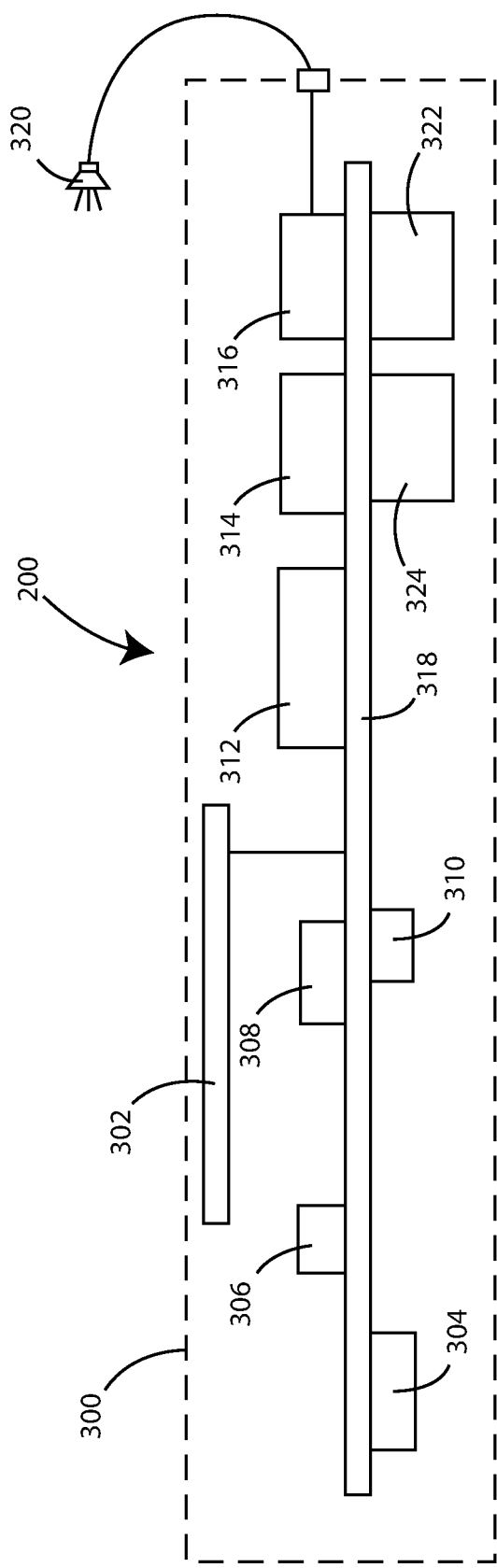
FIG. 3 is a schematic view of various components of a hearing assistance device in accordance with various embodiments herein.

Referring now to FIG. 3, a schematic block diagram is shown with various components of a hearing assistance device in accordance with various embodiments. The block diagram of FIG. 3 represents a generic hearing assistance device for purposes of illustration. The hearing assistance device 200 shown in FIG. 3 includes several components electrically connected to a flexible mother circuit 318 (e.g., flexible mother board) which is disposed within housing 300. A power supply circuit 304 can include a battery and can be electrically connected to the flexible mother circuit 318 and provides power to the various components of the hearing assistance device 200. In other examples, components of a hearing assistance device 200 may draw electrical power from another type of power source. One or more microphones 306 are electrically connected to the flexible mother circuit 318, which provides electrical communication between the microphones 306 and a digital signal processor (DSP) 312. Among other components, the DSP 312 incorporates or is coupled to audio signal processing circuitry configured to implement various functions described herein. A sensor package 314 can be coupled to the DSP 312 via the flexible mother circuit 318. The sensor package 314 can include one or more different specific types of sensors such as those described in greater detail below. One or more user switches 310 (e.g., on/off, volume, mic directional settings) are electrically coupled to the DSP 312 via the flexible mother circuit 318.

An audio output device 316 is electrically connected to the DSP 312 via the flexible mother circuit 318. In some embodiments, the audio output device 316 comprises a speaker (coupled to an amplifier). In other embodiments, the audio output device 316 comprises an amplifier coupled to an external receiver 320 adapted for positioning within an ear of a wearer. The external receiver 320 can include an electroacoustic transducer, speaker, or loud speaker. The hearing assistance device 200 may incorporate a communication device 308 coupled to the flexible mother circuit 318 and to an antenna 302 directly or indirectly via the flexible mother circuit 318. The communication device 308 can be a BLUETOOTH® transceiver, such as a BLE (BLUETOOTH® low energy) transceiver or other transceiver (e.g., an IEEE 802.11 compliant device). The communication device 308 can be configured to communicate with one or more external devices, such as those discussed previously, in accordance with various embodiments. In various embodiments, the communication device 308 can be configured to communicate with an external visual display device such as a smart phone, a video display screen, a tablet, a computer, a hologram, a virtual or augmented reality device, or the like. In various embodiments, the communication device 308 can be configured to communicate with one or more of the control system or navigation system of a vehicle. In various embodiments, the communication device 308 can be configured to communicate with one or more communication devices associated with a third party.

In various embodiments, the hearing assistance device 200 can also include a control circuit 322 and a memory storage device 324. The control circuit 322 can be in electrical communication with other components of the device. The control circuit 322 can execute various operations, such as those described herein. The control circuit 322 can include various components including, but not limited to, a microprocessor, a microcontroller, an FPGA (field-programmable gate array) processing device, an ASIC (application specific integrated circuit), or the like. The memory storage device 324 can include both volatile and non-volatile memory. The memory storage device 324 can include ROM, RAM, flash memory, EEPROM, SSD devices, NAND chips, and the like. The memory storage device 324 can be used to store data from sensors as described herein and/or processed data generated using data from sensors as described herein, including, but not limited to, information regarding exercise regimens, performance of the same, visual feedback regarding exercises, and the like.

Figure 4:
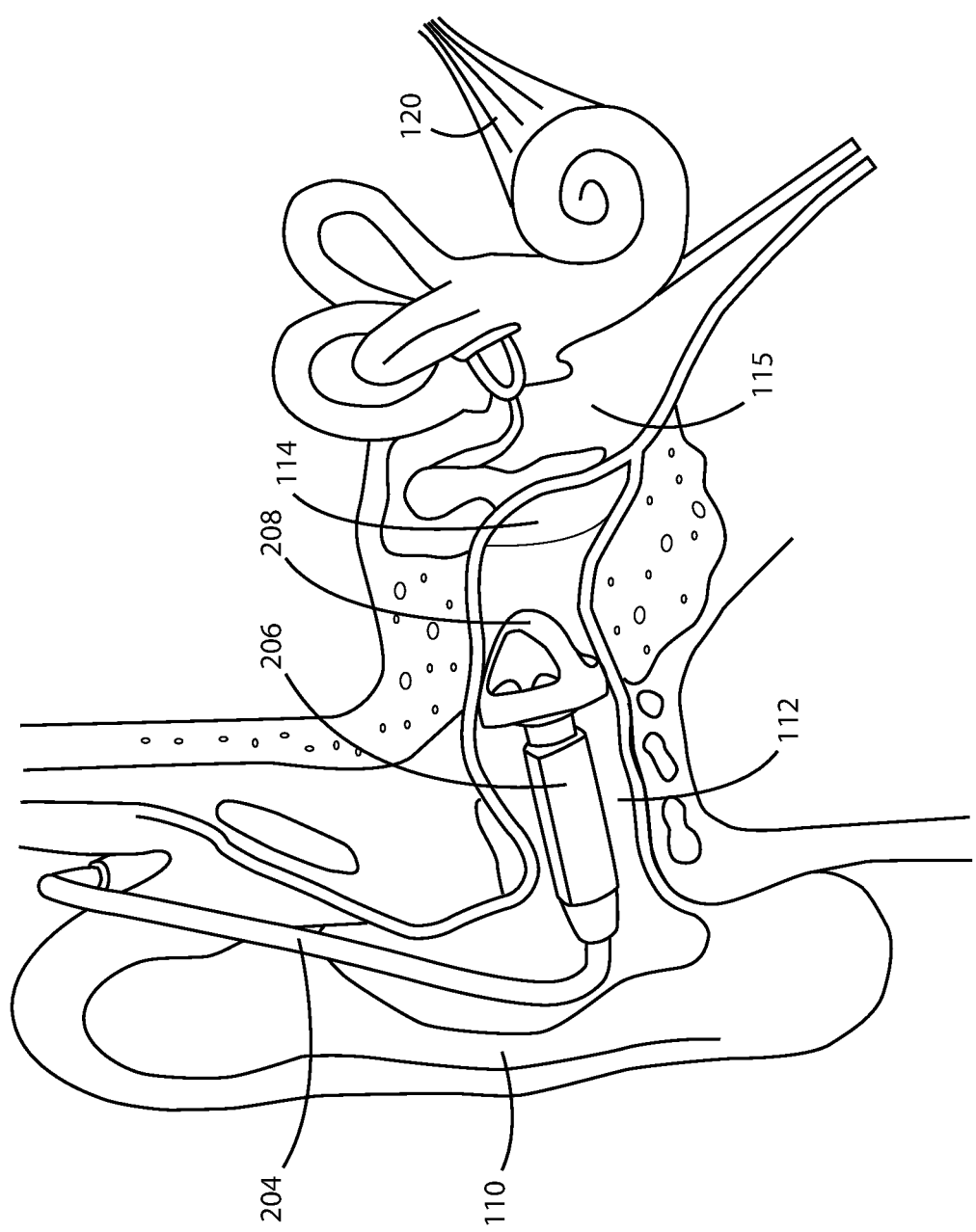
FIG. 4 is a schematic view of a hearing assistance device disposed within the ear of a subject in accordance with various embodiments herein.

As mentioned with regard to FIG. 2, the hearing assistance device 200 shown in FIG. 2 is a receiver-in-canal type device and thus the receiver is designed to be placed within the ear canal. Referring now to FIG. 4, a schematic view is shown of a hearing assistance device disposed within the ear of a subject in accordance with various embodiments herein. In this view, the receiver 206 and the earbud 208 are both within the ear canal 112, but do not directly contact the tympanic membrane 114. The hearing device housing is mostly obscured in this view behind the pinna 110, but it can be seen that the cable 204 passes over the top of the pinna 110 and down to the entrance to the ear canal 112.

While FIG. 4 shows a single hearing assistance device, it will be appreciated that subjects can utilize one or more hearing assistance devices such as two, with one for each ear. In some embodiments, the hearing assistance devices and sensors therein can be disposed on opposing lateral sides of the subject's head. Specifically, the hearing assistance devices and sensors therein can be disposed in a fixed position relative to the subject's head. In some embodiments, the hearing assistance devices and sensors therein can be disposed within opposing ear canals of the subject. In some embodiments, the hearing assistance devices and sensors therein can be disposed on or about opposing ears of the subject. The hearing assistance devices and sensors therein can be spaced apart from one another by a distance of at least 3, 4, 5, 6, 8, 10, 12, 14, or 16 centimeters and less than 40, 30, 28, 26, 24, 22, 20 or 18 centimeters, or by a distance falling within a range between any of the foregoing.

Figure 5:
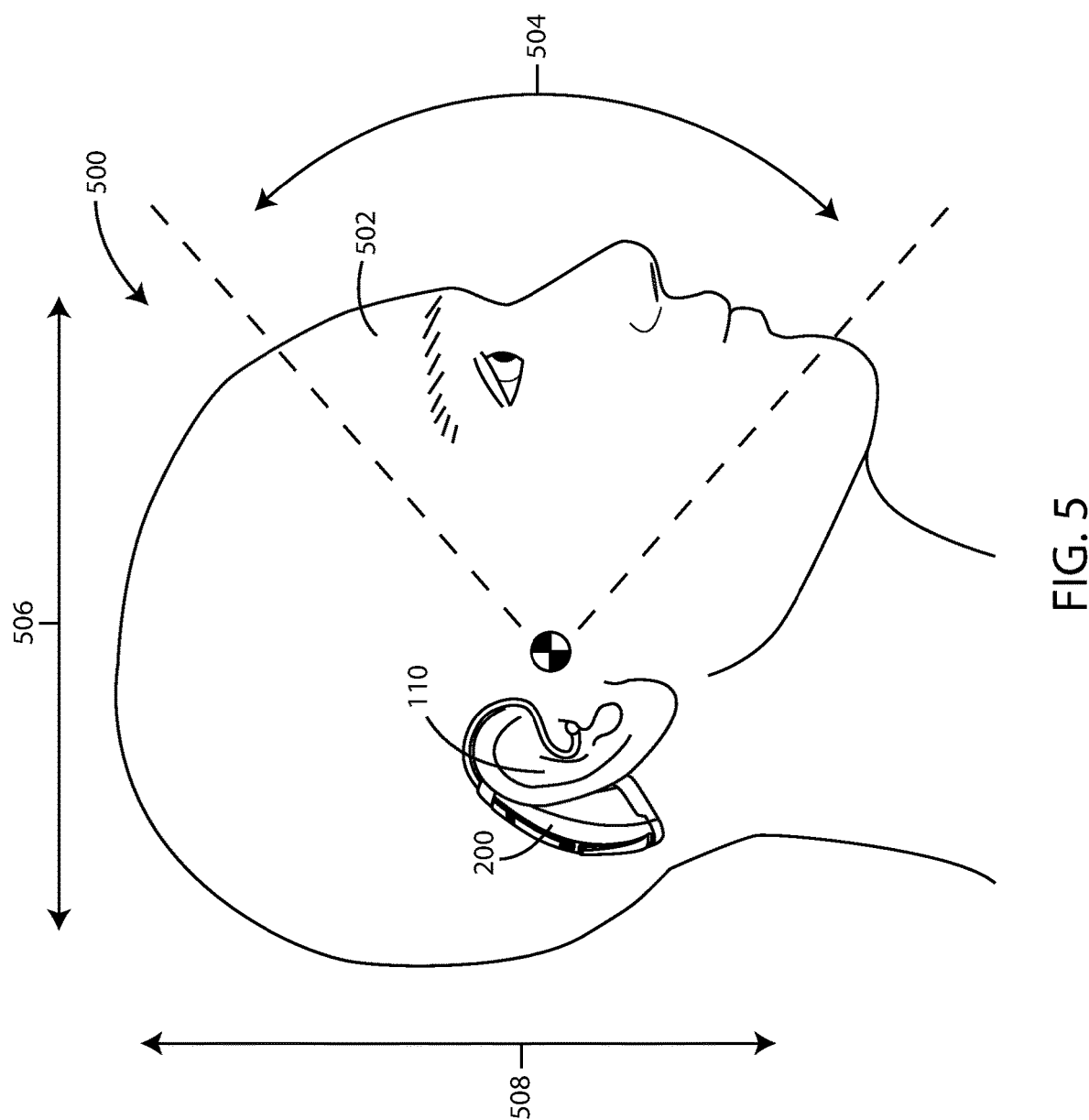
FIG. 5 is a schematic side view of a subject wearing a hearing assistance device in accordance with various embodiments herein.
Figure 6:
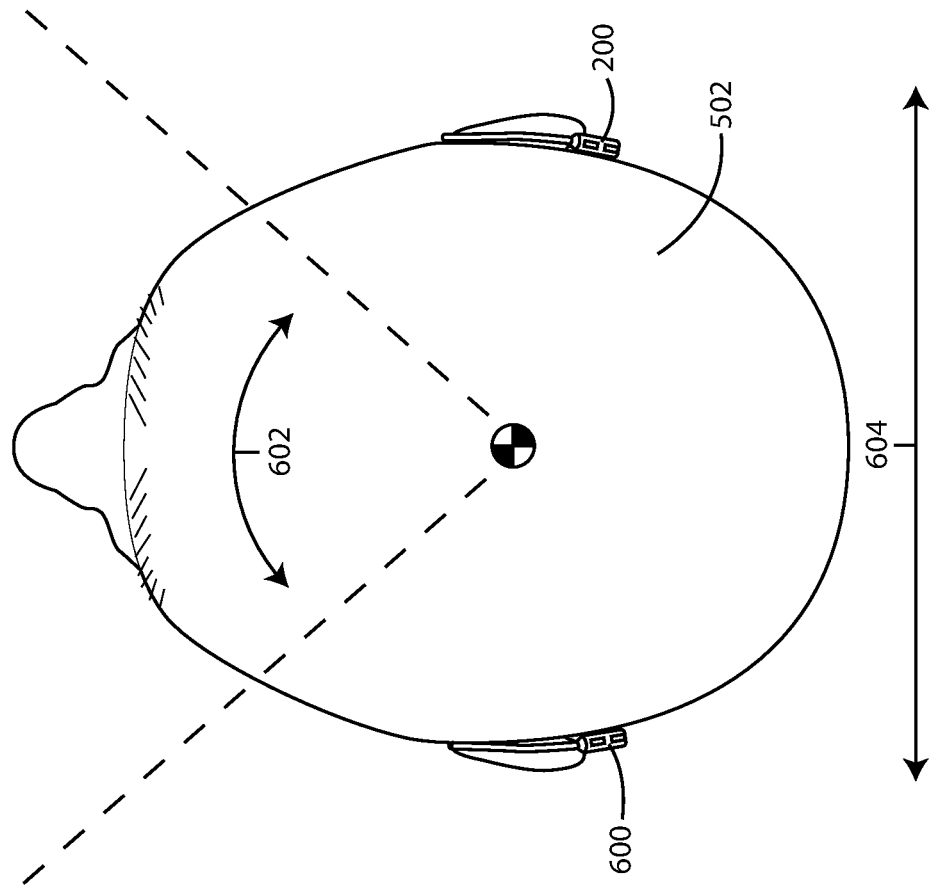
FIG. 6 is a schematic top view of a subject wearing a hearing assistance device in accordance with various embodiments herein.

Systems herein, and in particular hearing assistance devices herein, can include sensors (such as part of a sensor package 314) to detect movements of the subject wearing the hearing assistance device. Movements can be detected in any axis and can also specifically include rotation around any axis. Exemplary sensors are described in greater detail below. Referring now to FIG. 5, a schematic side view is shown of a subject 500 wearing a hearing assistance device 200 in accordance with various embodiments herein. For example, movements detected can include forward and/or backward movements 506 of the subject's head 502, upward and/or downward movements 508 of the subject's head 502, and rotational movements 504 of the subject's head 502 in a vertical plane. While FIG. 5 shows a single hearing assistance device, it will be appreciated that in various embodiments, subjects can wear two hearing assistance devices. Referring now to FIG. 6, a schematic top view is shown of a subject 500 wearing hearing assistance devices 200, 600 in accordance with various embodiments herein. Movements detected, amongst others, can also include side-to-side movements 604 of the subject's head 502, rotational movements 602 of the subject's head 502 in the horizontal plane, tilts to either side, and tilting of the subject's head 502 in the vertical plane.

As described above, embodiments of systems herein, such as hearing assistance devices, can track the motion or movement of a subject using a motion sensor. The head position of the subject can also be tracked. In various embodiments, the head position of the subject can be tracked simultaneously with tracking of the motion or movement of the subject. In various other embodiments, the position of other parts of the subject's body can also be tracked using operatively connected sensors distributed across the body (e.g., a body network of devices).

In some embodiments, the system can estimate visual system input based on the tracked head position. The system can estimate consistency between or otherwise compare the vestibular system inputs and the visual system inputs. In various embodiments, the system can also initiate responsive measures if the estimated consistency crosses a threshold value.

Figure 7:
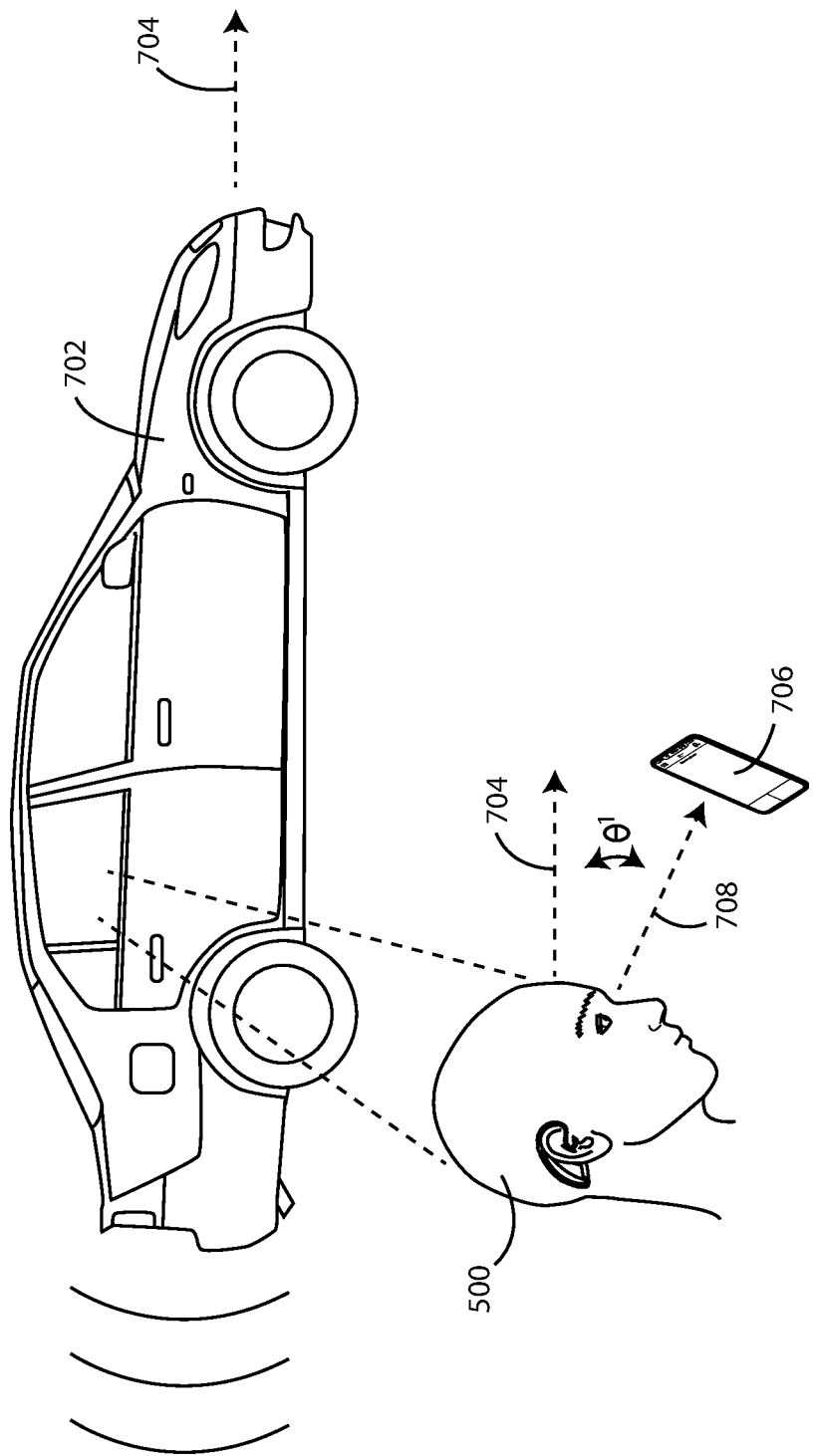
FIG. 7 is a schematic side view of a subject riding in a car in accordance with various embodiments herein.

Referring now to FIG. 7, a schematic side view is shown of a subject 500 riding in a car 702 in accordance with various embodiments herein. The car 702 can serve as a specific example of a vehicle. However, as used herein, the term "vehicle" shall include any machine that transports people including, but not limited to, wagons, bicycles, motor vehicles (motorcycles, cars, trucks, buses), railed vehicles (trains, trams), mobility assistance devices (e.g., wheelchairs, motorized wheelchairs, exoskeletons), self-balancing personal transporters, watercraft (ships, boats), amphibious vehicles (screw-propelled vehicle, hovercraft), aircraft (airplanes, helicopters, drones), agricultural and industrial equipment, and spacecraft.

In use, the car 702 can move predominantly in a particular direction of motion 704 at varying speeds. A subject 500 riding in the car 702 could experience visual system input that is largely consistent to vestibular system input, if they were looking straight ahead, such as if they were driving the car 702. However, particularly as a passenger, the subject 500 may be looking downward at a book or magazine, an external display device 706 such as a smartphone, an electronic game, or the like. In so doing, the subject's line of gaze 708 may deviate from the direction of motion 704. The subject's line of gaze 708 can be deemed to be a marker and/or proxy of visual system input in accordance with various embodiments herein. The direction of motion 704 can be deemed to be a marker and/or proxy of vestibular system input in accordance with various embodiments herein.

The direction of motion 704 can be determined by evaluating data from one or more sensors that are part of a sensor package 314 herein. By way of example, the direction of motion 704 can be determined by evaluating data from one or more motion sensors. The direction of motion 704 can also be determined by operatively connected sensors in the vehicle (which can be part of safety/guidance systems of the vehicle) in or on which the subject is riding (e.g., a signal from the vehicle reporting sensor data indicative of vehicle movement). The direction of motion 704 can also be determined by operatively connected sensors in another device, such as the smartphone of the user. In addition, future direction of motion can be predicted based upon maps, global positioning systems, navigation systems, and by the safety/guidance systems of the vehicle. Future direction of motion may also be predicted by monitoring the gaze (visual hotspots) of the wearer, of by head movements of the wearer (e.g., head tilting prior to a turn).

In various embodiments, the subject's line of gaze 708 can be determined by calculating the rotational position of the subject's head 502 with respect to gravity and/or with respect to the determined direction of motion 704. In various embodiments, the subject's line of gaze 708 can also be determined by tracking eye movement from an ear-level device. Exemplary techniques for tracking eye movement from an ear-level device are described in U.S. Pat. No. 9,167,356, issued Oct. 20, 2015, entitled ELECTROOCULOGRAM AS A CONTROL IN A HEARING ASSISTANCE DEVICE, the content of which is herein incorporated by reference. In various embodiments, the subject's line of gaze 708 can also be determined by using other operatively connected eye tracking devices, such as cameras facing an individual's eyes. The individual could be the subject or another individual such as one who is driving a vehicle (e.g., a subject as a passenger in the back of car can benefit from the direction determination/prediction that is enabled by tracking the eyes of the driver of a vehicle.

The subject's line of gaze 708 may deviate from the direction of motion 704 by angle $\Theta^1$. In accordance with various embodiments herein, the system can detect angle $\Theta^1$. In accordance with various embodiments herein, angle $\Theta^1$ can be used (by itself or in combination with other data inputs) to provide an estimation of inconsistency between visual system inputs and vestibular system inputs.

In some embodiments, the specific amount of degrees by which the subject's direction of gaze differs from the direction of movement (for example, angle $\Theta^1$) can be captured and used in an evaluation of consistency between vestibular system and visual system inputs. In some embodiments, evaluation of whether a specific threshold value has been crossed for the difference in direction between the subject's direction of gaze and the direction of movement can be used in an evaluation of consistency between vestibular system and visual system inputs. Threshold values can be about 1, 2, 3, 5, 7, 10, 15, 20, 25, 30, 35, 40, 45, 50, 60 degrees or more, or can be an amount falling within a range between any of the foregoing.

A subject's head tends to move over time. Thus, while angled downward $\Theta^1$ for a period of time, the subject may periodically reposition their head—(e.g. positioning at an upward angle then re-positioning at a downward angle). However, in some scenarios, transitory head movements may not impact motion sickness significantly. As such, in some embodiments, the amount of time and/or percentage of time that the subject's direction of gaze is at a particular angle with respect to the direction of movement can be tracked and evaluated in accordance with embodiments herein.

In some embodiments, a threshold may be set for a period of time during which the subject's direction of gaze deviates from the direction of movement before the deviation is considered as part of the evaluation of consistency between vestibular system and visual system inputs. In some embodiments, the threshold can be greater than or equal to 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 100, 110, 130, 180, 240 or 360 seconds, or can be an amount falling within a range between any of the foregoing.

In some embodiments, a histogram can be prepared including information on the total amount of time and/or percentage of time that the subject's direction of gaze deviates from the direction of movement by specific amounts or amount falling within specific ranges.

Figure 8:
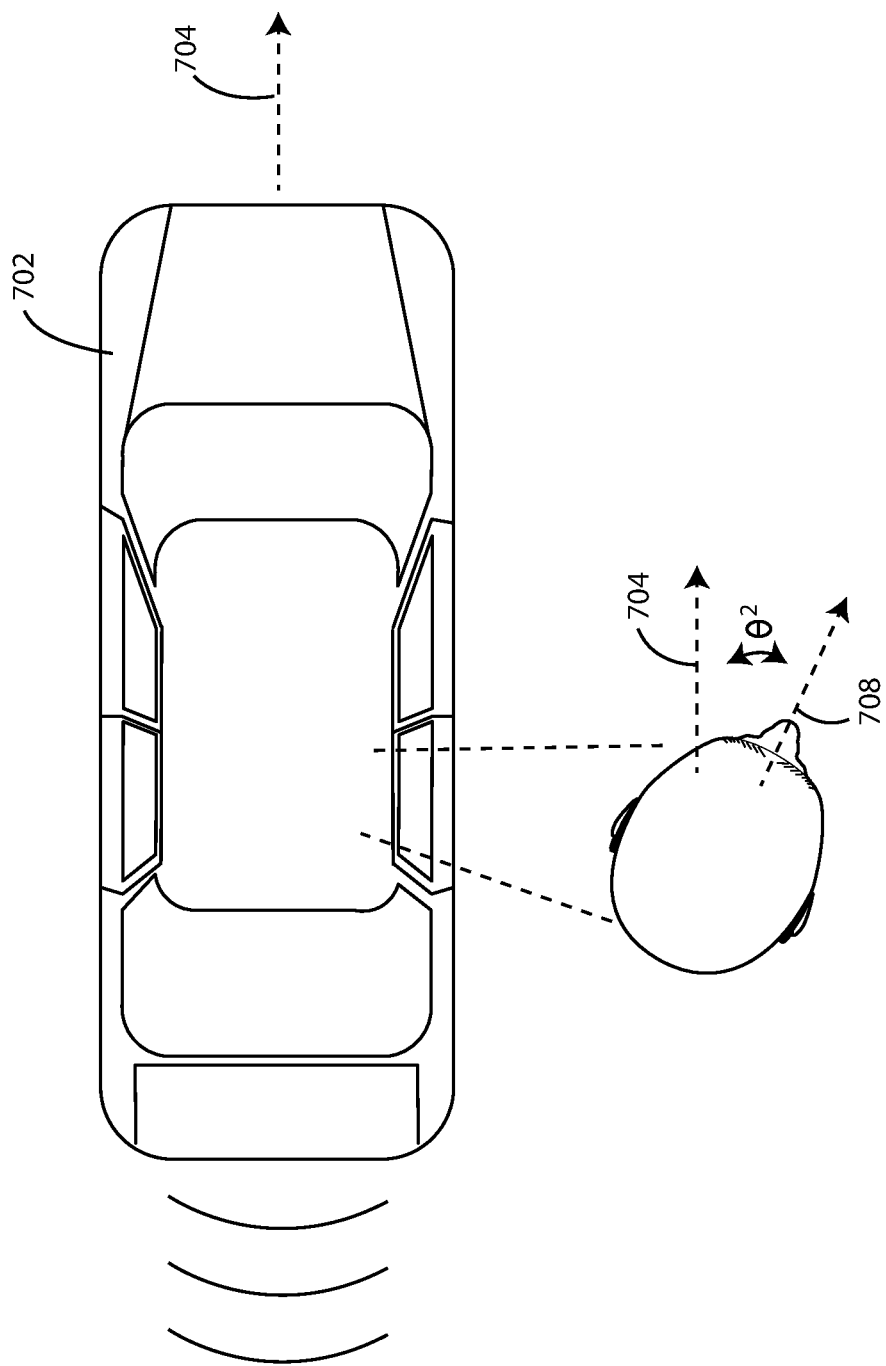
FIG. 8 is a schematic top view of a subject riding in a car in accordance with various embodiments herein.

It will be appreciated that a subject's line of gaze can be different than the direction of motion in other than a vertical dimension. For example, an individual riding in a vehicle may be looking to the side with respect to the direction of motion. Referring now to FIG. 8, a schematic top view is shown of a subject 500 riding in a car 702 in accordance with various embodiments herein.

The subject's line of gaze 708 may deviate from the direction of motion 704 in a horizontal plane by angle $\Theta^2$. In accordance with various embodiments herein, the system can detect angle $\Theta^2$. In accordance with various embodiments herein, angle $\Theta^2$ can be used as one element of an estimation of inconsistency between visual system inputs and vestibular system inputs.

In some embodiments, the specific amount of degrees by which the subject's direction of gaze differs from the direction of movement in the horizontal plane can be captured and used in an evaluation of consistency between vestibular system and visual system inputs. In some embodiments, whether or not the subject's direction of gaze differs from the direction of movement in the horizontal plane by at least a specific threshold value can be used in an evaluation of consistency between vestibular system and visual system inputs. Threshold values can be about 1, 2, 3, 5, 7, 10, 15, 20, 25, 30, 35, 40, 45, 50, 60, 70, 80 or 90 degrees or more, or can be an amount falling within a range between any of the foregoing. In some embodiments, the subject 500 could be seated backwards with respect to the direction of movement (such as when seated on a train). As such, in some embodiments, the threshold can be about 90, 100, 110, 120, 130, 140, 150, 160, 170 or 180 degrees, or an amount falling within a range between any of the foregoing.

A subject's head may tend to move over time. Thus, while angled in the vertical plan (to the side) $\Theta^2$ for a period of time, the subject may periodically move their head from side to side. As such, in some embodiments, the amount of time and/or percentage of time that the subject's direction of gaze is at a particular angle in the horizontal plane with respect to the direction of movement can be tracked and evaluated in accordance with embodiments herein.

In some embodiments, a threshold may be set for a period of time during which the subject's direction of gaze deviates from the direction of movement in the horizontal plane before the deviation is considered as part of the evaluation of consistency between vestibular system and visual system inputs. In some embodiments, the threshold can be greater than or equal to 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 100, 110, 130, 180, 240 or 360 seconds, or can be an amount falling within a range between any of the foregoing.

When a subject is riding in a vehicle and their head is angled downward, the subject's focal distance may be much different and much closer than if their head is up (in a neutral position) and they are looking in the direction of movement. For example, the subject's focal depth may be a distance of inches to feet (such as 8 inches to 3 feet) when focused on an object in the car versus a much greater distance (such as 10 yards to ∞) if their eyes are focused on objects outside the car in the direction the vehicle is traveling such as the road ahead and/or the horizon. In various embodiments herein, the subject's focal depth can be estimated based on factors including the current rotational position of their head in a vertical plane (e.g., head angled downward, level, or angled upward, and/or degree of same), current rotational position in a horizontal plane (e.g., looking to the side such as out a window or straight ahead), and, in some cases, information regarding the current surroundings of the subject (with can be identified/classified as described further below). For example, if the subject's head is angled down, but in the horizontal plane is straight ahead and the current surroundings are classified as a car, a bus, or a train, then it can be presumed that the current focal depth is on the order of 8 inches to 3 feet.

Motion sickness may be commonly experienced while a subject is riding in various types of vehicles. Some vehicles, in particular those for traversing water, can result in types of movement that is particularly likely to trigger motion sickness symptoms in some individuals. Systems in accordance with embodiments herein can be used to prevent and/or mitigate motion sickness in a subject riding in or on such vehicles.

Figure 9:
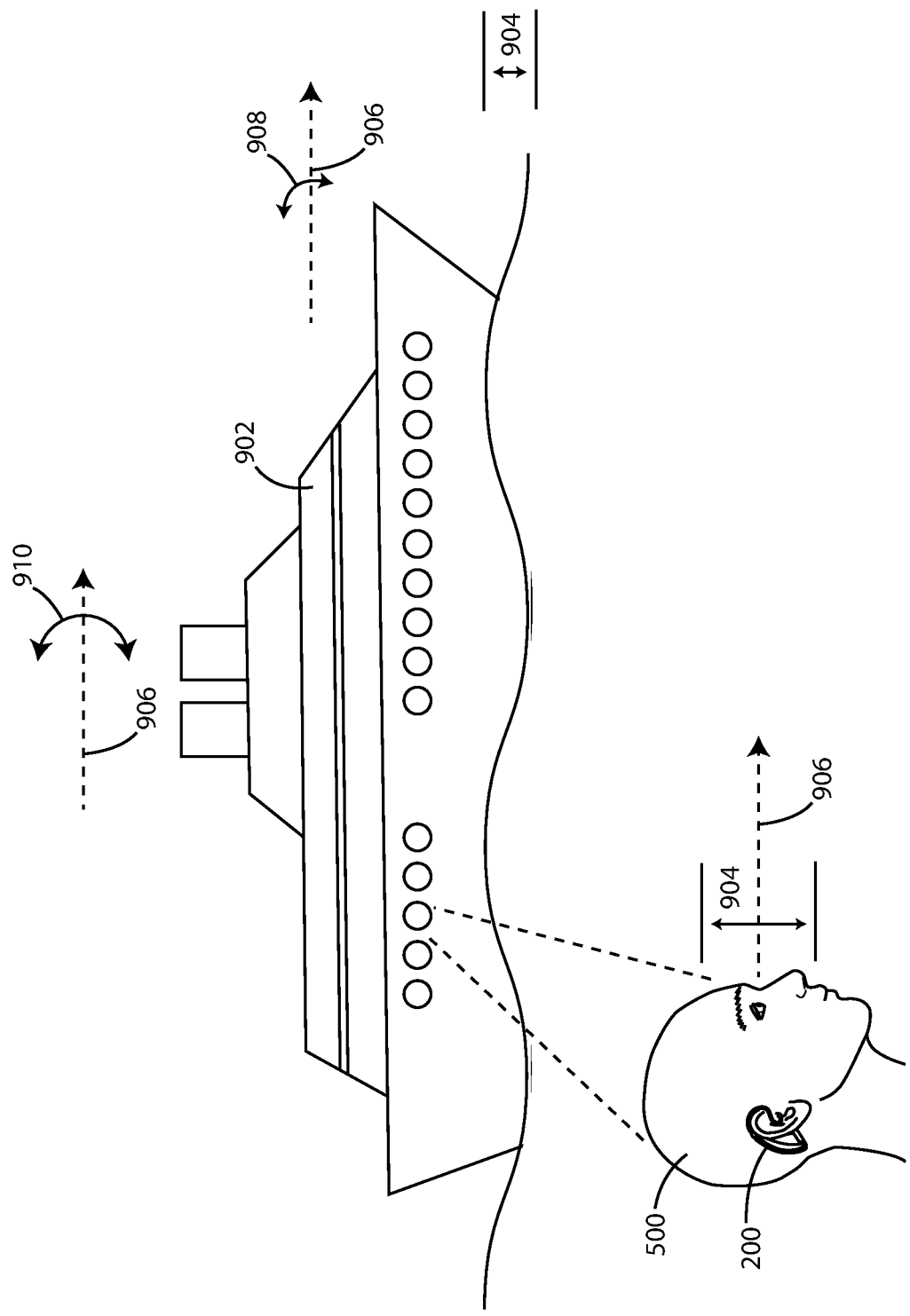
FIG. 9 is a schematic side view of a subject riding in a boat in accordance with various embodiments herein.

Referring now to FIG. 9, a schematic side view is shown of a subject 500 riding in a boat 902 in accordance with various embodiments herein. The boat 902 can move in a main direction of movement 906. However, the boat 902 can also move vertically 904. The boat 902 can also roll 908 and can pitch 910. As such, a subject 500 riding in or on the boat 902 can be subjected to movement vertically 904 as well as roll 908 and pitch 910. Simultaneously, the hearing assistance device(s) 200 and sensors therein can be used to track the position of the subject's head as well as the direction of motion 704, the subject's line of gaze 708, the degree and frequency of roll, the degree and frequency of pitch, the degree and frequency of vertical movement (such as vertical oscillating movement associated with a vehicle traversing water), and the like.

In various embodiments, external visual display devices can be used as part of systems and methods herein. The external visual display device can include a display screen and a camera. In some embodiments, the external visual display device can be a smartphone, a video monitor, a virtual reality display device, an augmented reality display device, or the like.

In some embodiments, the display screen can be a video touch screen. The display screen can display various pieces of information to the subject including, but not limited to, an indication that motion sickness inducing conditions have been detected, a query to the subject regarding how they feel, instructions for actions the subject should take to reduce the chances that they will experience motion sickness, instructions for action the subject should take to mitigate motion sickness if onset of the same has already occurred, a query to the subject regarding the effectiveness of a responsive measure, or the like.

The display screen can also provide the user with stimulation that allows the user to visualize motion in accordance with the user's vestibular system. For example, when the user is inside a moving vehicle, the inside of the vehicle may appear visually stationary to the user, which may be in disagreement with the vestibular input that the user may also be receiving. In at least one example, the system may display video images or an animation on a display screen of a device that simulates motion consistent with the motion of the user. Such images or an animation can also be displayed using a virtual or augmented reality display. The displayed video imagery may be further responsive to characteristics of the user's motion, such as changes in speed, changes in one or more of an altitude or distance relative to the surfaces approximate to the vehicle, changes in color, texture or lighting relative to the surfaces approximate to the vehicle, and the like. The displayed video imagery may be further responsive to predicted future changes of direction, speed, altitude, distance, surface characteristics, etc. of the vehicle. The displayed video imagery may be responsive to measured or reported severity of motion sickness symptoms. In addition, the display device may contain a motion sensor and dynamically adapt the perspective of the image being displayed, e.g., the motion simulation video or animation relative to the position of the display, itself. In at least one example, the display screen may show a video or animation that simulates motion in accordance with the motion of the user such that other displays (e.g., text, apps, games, images, videos, webpages, and the like) are overlaid/superimposed with a degree of opacity over top of the pictured video or animation simulation. Exemplary opacity values can be about 5%, 15%, 25%, 35%, 45%, 55%, 65%, 75%, 85%, or 95%, or can be an amount falling within a range between any of the foregoing. In at least one embodiment, the opacity of the overlay can be adjusted by the user. In at least one other embodiment, the opacity of the overlay may be dynamically adapted by one or more components of the system and/or control circuitry thereof. In some embodiments, a motion simulation video or animation may be presented to the user as a virtual or augmented reality.

A video processing circuit (which can be a part of a device with a display screen herein) can generate a 2D or 3D image based on information including one or more of geometry, viewpoint, texture, lighting and shading information, overlay graphics, and the like. In some embodiments, the video processing circuit can include a GPU (graphical processing unit). The term "graphics pipeline" or "view rendering pipeline" can be used to refer to the sequence of steps used to create 2D graphical images or 2D raster representations of a 3D scene. The video processing circuit and/or GPU can execute one or more steps of the graphics pipeline. The video processing circuit and/or GPU can also include one or more physical components used in the graphics pipeline. The graphics pipeline can include one or more stages of creating a scene out of geometric primitives, modelling and transformation, camera transformation, lighting, projection transformation, clipping, scan conversion or rasterization, and texturing and fragment shading. In various embodiments, other operations can also be performed. In various embodiments, the graphics pipeline can use OpenGL, DirectX, or other protocols.

The camera of the external visual display device can be positioned to face away from the display screen and back toward the subject. The camera can be used to capture an image or images of the subject's face and, in some cases, the subject's eyes. In some embodiments, the camera can be used to capture image(s) including the positioning of a subject's face, pupil, iris, and/or sclera. Such information can be used to calculate the direction of the subject's face and/or gaze. In some embodiments, such information can also be used to calculate angle, speed and direction of nystagmus. In some embodiments, information about nystagmus observed from the user's eyes may be used to further calculate or estimate the user's vestibular system inputs to the brain of the user. Aspects of nystagmus detection and characterization are described in commonly-owned U.S. Publ. Pat. Appl. No. 2018/0228404, the content of which is herein incorporated by reference. In some embodiments, such information can specifically be used to calculate the direction of the subject's face and/or gaze with respect to the camera. Aspects regarding such calculations are described in U.S. Publ. Appl. Nos. 2012/0219180 and 2014/0002586; the content of which is herein incorporated by reference.

Figure 10:
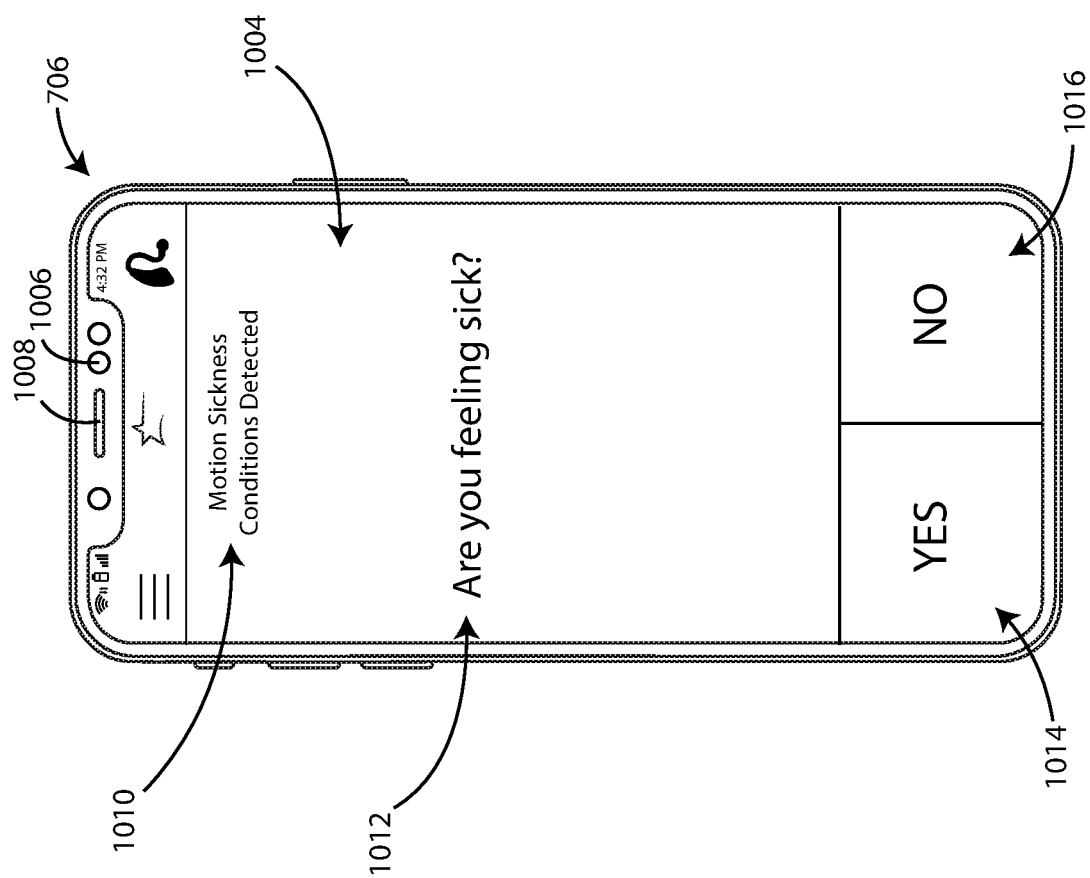
FIG. 10 is a schematic view of an external visual display device and elements of a display screen thereof in accordance with various embodiments herein.

Referring now to FIG. 10, a schematic view is shown of an external display device 706 and elements of a display screen 1004 thereof in accordance with various embodiments herein. The external display device 706 can include a camera 1006, a speaker 1008 and the like. Many visual display options are contemplated herein. In various embodiments, the external display device 706 can display an indicator 1010 or warning that conditions associated with motion sickness have been detected.

In various embodiments, the external display device 706 can display a query 1012 for the subject. For example, the query 1012 could relate to how the subject is currently feeling. In some embodiments, the system can be configured to display the query 1012 regarding how the subject is feeling after detecting conditions associated with motion sickness. In some embodiments, the external display device 706 can display virtual buttons 1014, 1016 (or input icons) to accept user input from the subject through the display screen 1004. It will be appreciated that queries to the subject can also be aural. For example, a hearing assistance device or an external device can present an auditory/verbal query. Also, feedback from the subject can be provided verbally or through gestures (e.g., head nodding, etc.) which can be detected by a microphone and/or motion sensors of the hearing assistance device or an external device.

In some embodiments, user input from the subject can regard at least one of a start, an end, a presence of, or an intensity of a motion sickness episode. In various embodiments herein, the estimation model for vestibular system input and visual system input can be altered based on the subject input. In various embodiments, the threshold value for consistency between the vestibular system input and the visual system input can be altered based on the user input from the subject.

In some embodiments, the system can detect emesis of the subject. Emesis can be detected based on characteristic acoustic patterns and/or characteristic postural and diaphragm/abdominal contraction patterns. In various embodiments, emesis can be detected by analyzing signals from at least one of an IMU and a microphone.

Methods

Various methods are included herein. Methods herein can include methods of preventing or mitigating motion sickness in a subject. Methods herein can include the execution of operations described elsewhere herein.

In a specific embodiment, a method of preventing or mitigating motion sickness in a subject is included herein. The method can include tracking motion of the subject using a first motion sensor. Exemplary motion sensors are described in greater detail below.

The method can further include estimating vestibular system input based on tracked motion of the subject. In some embodiments, an estimate of vestibular system input can be formed through applying a function relating tracked motion of the subject and vestibular system input. Aspects of the function can include one or more of the speed, velocity, consistency of speed and velocity, acceleration, consistency of acceleration, movement in directions other than the predominant direction of movement (e.g., such as bumps or other vertical or lateral movement experienced while riding in or on a vehicle), and the like. In some embodiments, the function relating tracked motion of the subject to vestibular system input can be derived empirically based on a population of subjects. In some embodiments, the function relating tracked motion of the subject to vestibular system input can be derived empirically based on a population of subjects with vestibular conditions similar to the subject using the device including factors relevant to motion sickness such as age, gender, health status, inner ear function, and the like. In some embodiments, the function relating tracked motion of the subject to vestibular system input can be derived through a calibration procedure executed with the subject using the device. By way of example, calibration can include prompting the subject to look at the horizon in the same direction as motion and/or looking above or below the horizon and/or at an angle with respect to the direction of motion. In various embodiments, the function can filter out movement having a frequency above a threshold value (digitally or using a low pass filter or the like).

In various embodiments, the method can also include tracking head position of the subject using the first motion sensor. Exemplary sensors used for tracking head position are described in greater detail below.

In various embodiments, the method can also include estimating visual system input based on tracked head position of the subject. In various embodiments, the method can also include estimating consistency between the vestibular system input and the visual system input. In various embodiments, the method can also include initiating responsive measures if the estimated consistency crosses a threshold value.

Sensors

Systems herein can include one or more sensor packages to provide data in order to determine aspects including, but not limited to, tracking movement of a subject and tracking head position of the subject. The sensor package can comprise one or a multiplicity of sensors. In some embodiments, the sensor packages can include one or more motion sensors amongst other types of sensors. Motion sensors herein can include inertial measurement units (IMU), accelerometers, gyroscopes, barometers, altimeters, and the like. Motions sensors can be used to track movement of a subject in accordance with various embodiments herein.

In some embodiments, the motion sensors can be disposed in a fixed position with respect to the head of a subject, such as worn on or near the head or ears. In some embodiments, the motion sensors can be disposed associated with another part of the body such as on a wrist, arm, or leg of the subject.

Sensor packages herein can also include one or more of a magnetometer, microphone, acoustic sensor, electrocardiogram (ECG), electroencephalography (EEG), eye movement sensor (e.g., electrooculogram (EOG) sensor), myographic potential electrode (EMG), heart rate monitor (photoplethysmogram, electrocardiogram, etc.), pulse oximeter, magnetic sensor, a telecoil, a wireless radio antenna, a barometer, thermometer, and the like.

In some embodiments, the sensor package can be part of a hearing assistance device. However, in some embodiments, the sensor packages can include one or more additional sensors that are external to a hearing assistance device. The one or more additional sensors can comprise one or more of an IMU, accelerometer, gyroscope, barometer, magnetometer, an acoustic sensor, eye motion tracker, EEG or myographic potential electrode (e.g., EMG), heart rate monitor (photoplethysmogram, electrocardiogram, etc.), and pulse oximeter. For example, the one or more additional sensors can include a wrist-worn or ankle-worn sensor package, a sensor package supported by a chest strap, or a sensor package in the form of a pendant that hangs from the neck. In some examples, the one or more additional sensors may be packaged as part of an accessory device to the hearing assistance device, such as a wireless audio streaming device, telephone or landline streamer, remote control, Direct Audio Input (DAI) gateway, remote microphone, telecoil receiver, captioning device, wearable or implantable health monitor, and combinations thereof.

The sensor package of a hearing assistance device can be configured to sense motion of the wearer. Data produced by the sensor(s) of the sensor package can be operated on by a processor of the device or system.

According to various embodiments, the sensor package can include one or more of an IMU, and accelerometer (3, 6, or 9 axis), a gyroscope, a barometer, an altimeter, a magnetometer, an eye movement sensor, a pressure sensor, an acoustic sensor, a heart rate sensor, an electrical signal sensor (such as an EEG, EMG or ECG sensor), a temperature sensor, a blood pressure sensor, an oxygen saturation sensor, an optical sensor, a thermometer, a global positioning system (GPS) sensor, and the like. In at least one embodiment, the sensor package may be integrated into the vehicle in/on which the user is riding and operatively connected to the hearing assistance device.

As used herein the term "inertial measurement unit" or "IMU" shall refer to an electronic device that can generate signals related to a body's specific force and/or angular rate. IMUs herein can include one or more of an accelerometer (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor can be, for example, an optical sensor, an infrared sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

The sensor package can include one or more sensors that are external to the hearing assistance device. In addition to the external sensors discussed hereinabove, the sensor package can comprise a network of body sensors (such as those listed above) that sense movement of a multiplicity of body parts (e.g., arms, legs, torso).

Surroundings Classification

In various embodiments of systems and methods herein, the system can classify the current surroundings of the subject. Classifying the current surroundings of the subject can be useful for purposes of selecting appropriate guidance to provide to the subject to prevent or treat symptoms of motion sickness. Classifying the current surroundings of the subject can also be useful for purposes of appropriately generating virtual or augmented reality visual and/or aural stimuli to prevent or treat symptoms of motion sickness. For example, when the user is in the car, a visual display can play a video animation depicting the road beneath the car, in motion relative to the movement of the vehicle/user. For example, an image of the road showing the painted lines passing beneath could be provided.

In various embodiments, the system can classify the current surroundings of the subject as one of vehicular, stationary, and non-vehicular, non-stationary. Vehicular surroundings can include car, truck, passenger vehicle, bus, train, plane, boat or the like. In many cases of vehicular surroundings causing motion sickness, the vestibular system may indicate movement, but the visual system may indicate no movement resulting in an inconsistency between the vestibular system input and the visual system input.

Examples of stationary surroundings can include a theater, a virtual reality environment, or the like. In many cases of stationary surroundings causing motion sickness, the vestibular system may indicate no movement, but the visual system may indicate movement is taking place. Non-vehicular, non-stationary surroundings can include, for example, a carnival ride, playground equipment, elevators/escalators, building sway, sports event participation, and the like. Examples of vehicular, stationary, and non-vehicular, non-stationary are shown below in Table 1.

TABLE 1

| Vehicular | Stationary | Non-Vehicular, Non-Stationary |
| --- | --- | --- |
| Passenger Vehicle (Car/Truck/Etc.) | VR Usage | Carnival Rides |
| Bus | Theater | Playground Equipment |
| Train | Presence in Front of Screen | Earthquake or Tremors |
| Plane | | Elevators/Escalators |
| Boat | | Moving walkways |
| | | Building Sway |
| | | Sporting Event Participation |

For the surroundings to be classified as vehicular, data inputs (including, but not limited to, sensor data) can be evaluated to determine whether they are consistent with the subject being in a vehicle. If the surroundings are non-consistent with a vehicular scenario, then the surroundings can be classified as either stationary or non-stationary. Exemplary data inputs consistent with vehicular, stationary, and non-vehicular, non-stationary are shown below in Table 2.

TABLE 2

| Vehicular | Stationary | Non-Vehicular, Non-Stationary |
| --- | --- | --- |
| Net Directional Motion Exceeding a Threshold Magnitude | Lack of Significant Net Directional Motion | Rotational Motion without Significant Net Directional Movement |
| Detection of Wireless Communication Signals Consistent with a Vehicle | Lack of Significant Rotational Movement | Oscillating Motion without Significant Net Directional Movement |
| Detection of Vibrations/Sounds Consistent with a Vehicle | Consistent Direction of Eye Gaze | Detection of Vibrations Consistent with a Non-Vehicular |
| Detection of Magnetic Fields Consistent with a Vehicle | Detection of Magnetic Fields Consistent with a Stationary Event | Event Detection of Magnetic Fields Consistent with a Non-Vehicle Event |

With regarding to vehicular surroundings, net directional motion can exceed a threshold magnitude of speed. For example, detecting net directional motion at a speed of greater than 10, 20, 30, 50, 75 or 100 m/s can be indicative of traveling in a vehicle. In some cases, wireless communication signals can be detected and can be used to classify the surroundings as vehicular. For example, in some cases the system can pickup BLUETOOTH® or WIFI® protocol communications and determine whether the same are consistent with a vehicle or vehicle navigation system.

In some cases, the system can further subclassify the surroundings. By way of example, if the surroundings are identified as being vehicular, the system can further identify a particular type or class of vehicle. This can be useful for purposes of selecting appropriate guidance to provide to the subject to prevent or treat symptoms of motion sickness.

In some cases, the system can detect vibrations and/or sounds that are consistent with vehicles, such as vibrations associated with an engine or movement of tires along pavement or a train along train tracks. By way of example, the frequencies of road noise associated with passenger vehicles generally display a prominent peak between 700 and 1300 Hz, and more particularly around 1000 Hz. By way of example, a train in motion applies moving steady loads to the railway track as well as dynamic excitation; this causes track deflections, vibration and noise. At generally lower frequencies than with passenger vehicles such as cars and trucks, the spectrum of measured track vibration has a distinct pattern, with spectral peaks occurring at multiples of the vehicle passing frequency. This pattern can be identified in order to classify the type of vehicle as a train.

In some embodiments, detection of sustained oscillating motion at a frequency of less than 20 Hz, 10 Hz, 5 Hz, 2 Hz, 1 Hz, or 0.5 Hz results in a classification of current surroundings as vehicular and a subclassification as a boat. In some embodiments, detection of sustained sound with a prominent peak at a frequency of less than 700, 500, 300, or 200 Hz results in a classification of current surroundings as vehicular and a subclassification as a train. In some embodiments, detection of sustained motion at a speed of greater than 120, 135, 150, 180, or 200 MPH results in a classification of current surroundings as vehicular and a subclassification as a plane. In some embodiments, detection of a change in altitude exceeding a threshold value over less than a threshold amount of time results in a classification of current surroundings as vehicular and a subclassification as a plane. In some embodiments, detection of altitude changes exceeding 300, 500, 750, 1000, or 1200 ft/min results in a classification of current surroundings as vehicular and a subclassification as a plane. In some embodiments, detection of altitude changes exceeding 300, 500, 750, 1000, or 1200 ft/min accompanied by a total altitude change of greater than 2000, 2500, 3000, 4000, 5000, 7500, or 10000 feet results in a classification of current surroundings as vehicular and a subclassification as a plane.

In some embodiments, the system can detect magnetic field strengths, frequencies, or patterns that are consistent with particular environments, including vehicles. By way of example, the electrical energy of a spark plug used in an internal combustion engine can create a detectable magnetic field. A detectable magnetic field of an automobile generally pulses at rate in accordance with the revolutions of the vehicle's engine. Under typical operating circumstances, a passenger vehicle has a periodic, wideband magnetic field pulse frequency of 50 to 350 times each second. The frequency spectrum of the magnetic field energy of a passenger vehicle typically exhibits several harmonics with a fundament frequency. Each vehicle has its own identifiable characteristic engine behavior which is influenced by how the vehicle's manufacturer has designed the operation of the engine, electric motor, drivetrain, alternator, ventilation system, onboard electronics, and the like.

Exemplary data inputs consistent with specific types/classes of vehicle are shown below in Table 3.

TABLE 3

| Passenger Vehicle | Bus | Train | Plane | Boat |
|---|---|---|---|---|
| Sound frequencies with prominent peak between 700 and 1300 Hz. | Sound frequencies with prominent peak between 700 and 1300 Hz. | Sound frequencies with prominent peak below 500 Hz. | Net directional motion greater than 150 mph; Altitude changes exceeding 500 ft/min | Low frequency oscillating motion (pitch, roll, vertical oscillation); Net directional motion less than 20 m/s. |

Responsive and/or Preventative Measures

The system can be configured to initiate responsive measures if conditions for motion sickness are detected. The system can be configured to initiate responsive measures if the estimated consistency between the vestibular system input and the visual system input crosses a threshold value.

In various embodiments, the responsive measures can include prompting the subject to move their head sufficiently to increase consistency between the vestibular system input and the visual system input. In various embodiments, the responsive measure can include lifting the subjects head to a horizontal position if the tracked head position is indicated to be below or above horizontal. In various embodiments, the responsive measure can include administering aural stimulation to the subject. In various embodiments, the responsive measure can include prompting the subject to open a vent and/or adjust a fan speed to increase air flow. In various embodiments, the responsive measure can include prompting the subject to maintain their gaze at a fixed point. In various embodiments, the responsive measure can include prompting the subject to maintain their gaze at a fixed point on the horizon no less than 30 degrees different than the direction of a vector representing their current motion. In various embodiments, the responsive measure can include prompting, pacing, or otherwise assisting the subject to breath according to a predetermined cadence. In some embodiments, the predetermined cadence can be less than or equal to 18, 16, 14, 12, 10, 8, 6, or 4 breaths per minute, or can be an amount falling within a range between any of the foregoing.

In various embodiments, the responsive measures can include providing auditory stimulation. In various embodiments, auditory stimulation can include a perceptually stationary auditory stimulus. In various embodiments, the responsive measures can include prompting the subject to focus their gaze on the horizon. In various embodiments, can use tracked head position of the subject to assess whether the subject focused their gaze on the horizon.

In accordance with various embodiments herein, hearing assistance device(s) that can be configured to guide the wearer of a hearing assistance device through a prescribed series of body movements or actions in accordance with a predetermined corrective or therapeutic maneuver, physical therapy or exercise routine. A maneuver, physical therapy or exercise routine involves a prescribed series of body movements or actions that can be implemented by the wearer of a hearing assistance device in an attempt to correct or treat a physiologic disorder or execute a physical fitness routine. Exercises (or routines or maneuvers herein) can include, but are not limited to, habituation exercises, gaze stabilization exercises, and balance training exercises. Exercises can include a series of actions including one or more of turning their head in a specified direction by a specified amount, moving their head in a specific direction by a specified amount, focusing their gaze on a stationary or moving point, assuming different postures, etc.

Guidance and/or feedback herein can include auditory guidance, visual guidance, or auditory and visual guidance. Audio guidance can include any one or a combination of different sounds, such as tones, noise bursts, human speech, animal/natural sounds, synthesized sounds, and music, among other sounds.

In some embodiments, a virtual audio interface can be used to provide auditory stimulation to a subject. The virtual audio interface can be configured to synthesize three-dimensional (3-D) audio that guides the wearer in performing specific physical movements of a predetermined corrective or therapeutic maneuver, physical therapy or exercise routine. In specific, the virtual audio interface can be configured to synthesize three-dimensional (3-D) audio that guides the wearer to perform physical movements to prevent and/or alleviate symptoms of motion sickness. For example, a synthesized 3-D virtual audio target can be generated at the specified location relative to the wearer's current head position. In response, the wearer moves his or her head in the specified direction indicated by the audio target.

According to some embodiments, the virtual audio interface can generate audio cues comprising spatialized 3-D virtual sound emanating from virtual spatial locations that serve as targets for guiding wearer movement. In some embodiments, the spatialized 3-D virtual sound can be generated so as to be perceived by the wearer as emanating from the horizon. The horizon is perpendicular to the direction of gravity. The direction of gravity can be measured by accelerometer as a constant bias in that direction. Therefore, signals from the accelerometer can be used to determine the location of the horizon.

The wearer can execute a series of body movements in a direction and/or extent indicated by a sequence of virtual sound targets. The sound generated at the virtual spatial locations can be any broadband sound, such as complex tones, noise bursts, human speech, music, etc. or a combination of these and other types of sound. In various embodiments, the virtual audio interface is configured to generate binaural or monaural sounds, alone or in combination with spatialized 3-D virtual sounds. The binaural and monaural sounds can be any of those listed above including single-frequency tones.

In other embodiments, the virtual audio interface is configured to generate human speech that guides the wearer in performing specific physical movements of a predetermined corrective or therapeutic maneuver, such as to prevent or alleviate motion sickness. The speech can be synthesized speech or a pre-recording of real speech. In embodiments that employ a single hearing assistance device (for one ear), for example, the virtual audio interface generates monaural sound in the form of speech, which can be accompanied by other sounds, such as single or multi-frequency tones, noise bursts or music. In embodiments that employ two hearing assistance devices (one device for each ear), the virtual audio interface can generate monaural or binaural sound in the form of speech, which can be accompanied by other sounds, such as single or multi-frequency tones, noise bursts or music. The virtual audio interface can display (play back) spoken instructions to guide the wearer though specific physical movements of a predetermined corrective or therapeutic maneuver, physical therapy or exercise routine. Further aspects of virtual audio interfaces are described in commonly owned U.S. patent application Ser. No. 15/589,298, titled "Hearing Assistance Device Incorporating Virtual Audio Interface for Therapy Guidance", the content of which is herein incorporated by reference in its entirety. Exemplary speech can include instructions for the wearer to "focus eyes on the horizon", "pickup your head", "look straight ahead", and the like.

In some examples, systems herein can apply a machine learning algorithm using reinforcement machine learning techniques to select the best possible responsive measure for one or more of the user or a context regarding the user (e.g., vehicle, non-vehicle, stationary, etc.). Reinforcement learning models can consider one or more of a data input, data classification, data output, responsive measure, guidance, feedback, response to queries, and the like. In one or more examples, the reinforcement machine learning model(s) can further consider the statistical data associated with historical data (e.g., data stored in a data storage system) to optimize the responsive measure. In one or more embodiments herein, determining a responsive measure includes applying input data to a statistical model or module. Such a statistical model or module can be developed from evaluating the effectiveness of responsive measures of the hearing assistance device(s) over time.

Further Embodiments

In an embodiment, a method of preventing or mitigating motion sickness in a subject is included, the method including tracking motion of the subject using a first motion sensor, estimating a vestibular system input based on tracked motion of the subject, tracking head position of the subject using the first motion sensor, estimating a visual system input based on tracked head position of the subject, estimating consistency between the vestibular system input and the visual system input, and initiating a responsive measure if the estimated consistency crosses a threshold value.

In an embodiment, the responsive measure can include prompting the subject to move their head sufficiently to increase consistency between the vestibular system input and the visual system input.

In an embodiment, the responsive measure can include providing auditory stimulation.

In an embodiment, the auditory stimulation can include a perceptually stationary auditory stimulus.

In an embodiment, the responsive measure can include prompting the subject to focus their gaze on the horizon.

In an embodiment, the method can further include using tracked head position of the subject to assess whether the subject focused their gaze on the horizon.

In an embodiment, the responsive measure can include displaying video images on a device with a display screen showing motion consistent with tracked motion.

In an embodiment, the shown motion changes in response to tracked motion changes.

In an embodiment, estimating visual system input based on tracked head position of the subject includes estimating a direction of visual focus of the subject.

In an embodiment, a method further can include estimating focal depth of the subject.

In an embodiment, a method further can include tracking eye movement of the subject.

In an embodiment, estimating vestibular system input based on tracked motion of the subject includes estimating a motion vector.

In an embodiment, a method further includes estimating vestibular system input based on tracked motion of the subject and tracked head position of the subject.

In an embodiment, a method further can include querying the subject regarding their status if the estimated consistency crosses a threshold value.

In an embodiment, a method further can include querying the subject regarding their status if the estimated consistency crosses a threshold value for a threshold amount of time.

In an embodiment, a method further can include sensing ambient sounds with a microphone as part of a hearing assistance device and classifying current surroundings of the subject based on the ambient sounds.

In an embodiment, a method further can include sensing data with at least one of a magnetic sensor, a telecoil, a wireless radio antenna, and a motion sensor as part of a hearing assistance device and classifying current surroundings of the subject based on the ambient sounds.

In an embodiment, a method further can include sensing data with at least one sensor and further can include classifying the current surroundings as one of vehicular, stationary, and non-stationary.

In an embodiment, a method further can include subclassifying vehicular surroundings as one of a passenger vehicle, a bus, a train, a plane, and a boat.

In an embodiment, a method further can include detecting motion at a frequency of less than 10 Hz.

In an embodiment, a method further can include detecting motion at a frequency of less than 2 Hz.

In an embodiment, a method further can include detecting motion at a frequency of less than 0.5 Hz.

In an embodiment, detection of sustained oscillating motion at a frequency of less than 0.5 Hz results in a classification of current surroundings as vehicular and a subclassification as a boat.

In an embodiment, a method further can include detecting ambient sound, wherein detection of sustained sound at a frequency of less than 200 Hz results in a classification of current surroundings as vehicular and a subclassification as a train.

In an embodiment, detection of sustained motion at a speed of greater than 150 MPH results in a classification of current surroundings as vehicular and a subclassification as a plane.

In an embodiment, detection of a change in altitude exceeding a threshold value over less than a threshold amount of time results in a classification of current surroundings as vehicular and a subclassification as a plane.

In an embodiment, the change in altitude is detected with a barometer.

In an embodiment, a method further can include accepting a subject input regarding at least one of a start, an end, a presence of, or an intensity of a motion sickness episode.

In an embodiment, a method further can include detecting emesis of the subject.

In an embodiment, emesis is detected using at least one of an IMU and a microphone.

In an embodiment, a method further can include altering an estimation model for vestibular system input and visual system input based on the subject input.

In an embodiment, a method further can include altering a threshold value for consistency between the vestibular system input and the visual system input based on the subject input.

In an embodiment, a method further can include calibrating the first motion sensor including prompting the subject to look at the horizon.

In an embodiment, the first motion sensor is disposed in a fixed position relative to the subject's head.

In an embodiment, a method further can include tracking motion of the subject using a second motion sensor and tracking head position of the subject using the second motion sensor.

In an embodiment, the first motion sensor and the second motion sensor are disposed on opposing lateral sides of the subject's head.

In an embodiment, the first motion sensor and the second motion sensor are disposed on or about opposing ears of the subject.

In an embodiment, the first motion sensor is mounted in a first hearing assistance device and the second motion sensor is mounted in a second hearing assistance device.

In an embodiment, the first motion sensor can include an IMU.

In an embodiment, a method of preventing or mitigating motion sickness in a subject is included, the method can include tracking motion of the subject using a first motion sensor associated with a hearing assistance device, tracking head position of the subject using the first motion sensor, sensing ambient sounds with the hearing assistance device, classifying the surroundings based on the tracked motion, tracked head position, and ambient sound as one of vehicular, stationary, and non-stationary, initiating a responsive measure based on the classification of the surroundings.

In an embodiment, a responsive measure can include lifting the subjects head to a horizontal position if the tracked head position is indicated to be below or above horizontal.

In an embodiment, a responsive measure can include administering aural stimulation to the subject.

In an embodiment, a responsive measure can include prompting the subject to open a vent and/or adjust a fan speed to increase air flow.

In an embodiment, a responsive measure can include prompting the subject to maintain their gaze at a fixed point.

In an embodiment, a responsive measure can include prompting the subject to maintain their gaze at a fixed point on the horizon no less than 30 degrees different than the direction of a vector representing their current motion.

In an embodiment, a responsive measure can include prompting the subject to breath according to a predetermined cadence.

In an embodiment, a method further can include subclassifying a vehicular classification based on at least one of the tracked motion, tracked head position, vibrations, ambient sound and magnetic field as one of: a passenger vehicle, a bus, a train, a plane, and a boat.

In an embodiment, a motion sickness prevention system is included having a control circuit, a motion sensor in electrical communication with the control circuit, wherein the motion sensor is disposed in a fixed position relative to a head of a subject wearing the hearing assistance device, a microphone in electrical communication with the control circuit, an electroacoustic transducer for generating sound in electrical communication with the control circuit, a power supply circuit in electrical communication with the control circuit, wherein the control circuit is configured to track motion of the subject using the motion sensor, estimate vestibular system input based on tracked motion of the subject, track head position of the subject using the motion sensor, and estimate visual system input based on tracked head position of the subject.

In an embodiment, a motion sickness prevention system is included having a control circuit, a motion sensor in electrical communication with the control circuit, wherein the motion sensor is disposed in a fixed position relative to a head of a subject wearing the hearing assistance device, a microphone in electrical communication with the control circuit, an electroacoustic transducer for generating sound in electrical communication with the control circuit, a power supply circuit in electrical communication with the control circuit, wherein the control circuit is configured to track motion of a subject using the motion sensor, track head position of a subject using the motion sensor, sense vibrations with a vibration sensor, sense ambient sounds with the microphone, sense magnetic fields with a magnetic field sensor, and classify the surroundings based on the tracked motion, tracked head position, sensed vibrations, sensed ambient sound, and sensed magnetic fields, as one of vehicular, stationary, and non-stationary, wherein the control circuit in further configured to initiate a responsive measure based on the classification of the surroundings.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method of preventing or mitigating motion sickness in a subject comprising:
    tracking motion of the subject using a first motion sensor;
    estimating a vestibular system input based on tracked motion of the subject, wherein estimating the vestibular system input comprises estimating a direction of motion of the subject;
    tracking head position of the subject using the first motion sensor;
    estimating a visual system input based on tracked head position of the subject, wherein estimating the visual system input comprises estimating a line of gaze of the subject;
    estimating consistency between the vestibular system input and the visual system input by calculating an angle between the line of gaze and the direction of motion;
    comparing the calculated angle to a threshold value; and
    initiating a responsive measure if the estimated consistency crosses the threshold value.

2. The method of claim 1, the responsive measure comprising prompting the subject to move their head sufficiently to increase consistency between the vestibular system input and the visual system input.

3. The method of claim 1, the responsive measure comprising providing auditory stimulation.

4. The method of claim 3, the auditory stimulation comprising a perceptually stationary auditory stimulus.

5. The method of claim 1, the responsive measure comprising prompting the subject to focus their gaze on the horizon.

6. The method of claim 5, further comprising using tracked head position of the subject to assess whether the subject focused their gaze on the horizon.

7. The method of claim 1, the responsive measure comprising displaying video images on a device with a display screen showing motion consistent with tracked motion.

8. The method of claim 7, wherein the shown motion changes in response to tracked motion changes.

9. The method of claim 1, wherein estimating visual system input based on tracked head position of the subject comprises estimating a direction of visual focus of the subject.

10. The method of claim 1, further comprising estimating focal depth of the subject.

11. The method of claim 1, further comprising tracking eye movement of the subject.

12. The method of claim 1, further comprising sensing ambient sounds with a microphone as part of a hearing assistance device and classifying current surroundings of the subject based on the ambient sounds.

13. The method of claim 1, further comprising sensing data with at least one of a magnetic sensor, a telecoil, a wireless radio antenna, and a motion sensor as part of a hearing assistance device and classifying current surroundings of the subject based on ambient sounds.

14. The method of claim 1, further comprising sensing data with at least one sensor and further comprising classifying current surroundings as one of vehicular, stationary, and non-stationary.

15. The method of claim 14, further comprising subclassifying vehicular surroundings as one of a passenger vehicle, a bus, a train, a plane, and a boat.

16. The method of claim 15, further comprising detecting ambient sound, wherein detection of sustained sound at a frequency of less than 200 Hz results in a classification of current surroundings as vehicular and a subclassification as a train.

17. The method of claim 15, wherein detection of sustained motion at a speed of greater than 150 MPH results in a classification of current surroundings as vehicular and a subclassification as a plane.

18. The method of claim 15, wherein detection of a change in altitude exceeding a threshold value over less than a threshold amount of time results in a classification of current surroundings as vehicular and a subclassification as a plane.

19. The method of claim 1, further comprising detecting motion at a frequency of less than 0.5 Hz; wherein detection of sustained oscillating motion at a frequency of less than 0.5 Hz results in a classification of current surroundings as vehicular and a subclassification as a boat.

20. The method of claim 1, further comprising detecting emesis of the subject.

21. A method of preventing or mitigating motion sickness in a subject comprising:
    tracking a direction of motion of the subject using a first motion sensor associated with a hearing assistance device;
    tracking a line of gaze of the subject using the first motion sensor;
    calculating an angle between the line of gaze and the direction of motion;
    sensing ambient sounds with the hearing assistance device;
    classifying surroundings based on the tracked motion, tracked head position, and ambient sounds as one of
        vehicular;
        stationary; and
        non-stationary; and
    initiating a responsive measure based on the classification of the surroundings and the calculated angle.

22. The method of claim 21, the responsive measure comprising lifting the subject's head to a horizontal position if the tracked line of gaze is indicated to be below or above horizontal.

23. The method of claim 21, the responsive measure comprising at least one of
    administering aural stimulation to the subject;
    prompting the subject to open a vent and/or adjust a fan speed to increase air flow;
    prompting the subject to maintain their gaze at a fixed point;
    prompting the subject to maintain their gaze at a fixed point on a horizon no less than 30 degrees different than a direction of a vector representing their current motion; and
    prompting the subject to breath according to a predetermined cadence.

* * * * *